(12) United States Patent
Hayashi et al.

(10) Patent No.: US 7,972,269 B2
(45) Date of Patent: Jul. 5, 2011

(54) ULTRASONOGRAPHIC DEVICE AND ULTRASONOGRAPHIC METHOD

(75) Inventors: Tetsuya Hayashi, Chiba (JP); Hiroshi Kanda, Saitama (JP); Osamu Arai, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 81 days.

(21) Appl. No.: 10/565,435

(22) PCT Filed: Jul. 21, 2004

(86) PCT No.: PCT/JP2004/010321
§ 371 (c)(1),
(2), (4) Date: Jan. 20, 2006

(87) PCT Pub. No.: WO2005/006987
PCT Pub. Date: Jan. 27, 2005

(65) Prior Publication Data
US 2006/0241458 A1    Oct. 26, 2006

(30) Foreign Application Priority Data
Jul. 22, 2003   (JP) ................. 2003-200162

(51) Int. Cl.
*A61B 8/00* (2006.01)
*A61B 8/06* (2006.01)

(52) U.S. Cl. ......... 600/443; 600/465; 600/468; 600/453

(58) Field of Classification Search .................. 600/465, 600/453, 468, 454; 324/201
See application file for complete search history.

(56) References Cited

U.S. PATENT DOCUMENTS

| RE35,371 | E  | * | 11/1996 | Seo ............................... 600/455 |
| 6,116,244 | A  | * | 9/2000 | Hossack et al. ............... 600/441 |
| 6,176,832 | B1 | * | 1/2001 | Habu et al. .................... 600/485 |
| 6,239,796 | B1 | * | 5/2001 | Alexander ..................... 715/809 |
| 6,258,029 | B1 | * | 7/2001 | Guracar et al. ................ 600/443 |
| 6,544,181 | B1 | * | 4/2003 | Buck et al. ..................... 600/455 |
| 6,547,736 | B1 | * | 4/2003 | Moehring et al. ............. 600/454 |
| 6,582,370 | B2 | * | 6/2003 | Jibiki .............................. 600/455 |
| 6,610,014 | B1 | * | 8/2003 | Yamamoto et al. ........... 600/453 |

(Continued)

FOREIGN PATENT DOCUMENTS

JP    11-299784    11/1999

(Continued)

OTHER PUBLICATIONS

International Search Report issued in corresponding PCT/JP2004/010321.

(Continued)

*Primary Examiner* — Long V Le
*Assistant Examiner* — Helene Bor
(74) *Attorney, Agent, or Firm* — Antonelli, Terry, Stout & Kraus, LLP.

(57) ABSTRACT

An ultrasound diagnostic apparatus including: a tomogram forming means forming a tomogram of a diagnosis portion of an examinee by transmitting/receiving an ultrasound wave to/from the examinee via an ultrasound probe; color Doppler image forming means forming a color Doppler image based on a Doppler signal obtained from the diagnosis portion; image processing means performing image processing on the tomogram and the color Doppler image; and display means displaying images obtained by the image processing means, the tomogram and the color Doppler image being color displayed on the display means, wherein the image processing means causes the color Doppler image to be displayed transparently.

18 Claims, 6 Drawing Sheets

U.S. PATENT DOCUMENTS

| | | | | |
|---|---|---|---|---|
| 6,616,611 B1* | 9/2003 | Moehring | | 600/454 |
| 6,735,463 B2* | 5/2004 | Izatt et al. | | 600/476 |
| 7,044,913 B2* | 5/2006 | Shiki | | 600/454 |
| 7,128,713 B2* | 10/2006 | Moehring et al. | | 600/453 |
| 7,201,715 B2* | 4/2007 | Burdette et al. | | 600/3 |
| 2003/0023153 A1* | 1/2003 | Izatt et al. | | 600/407 |
| 2004/0102706 A1* | 5/2004 | Christopher et al. | | 600/453 |
| 2004/0249293 A1* | 12/2004 | Sandler et al. | | 600/481 |
| 2005/0090747 A1* | 4/2005 | Clark | | 600/453 |
| 2005/0131300 A1* | 6/2005 | Bakircioglu et al. | | 600/453 |

FOREIGN PATENT DOCUMENTS

JP            2000-000238            1/2000

OTHER PUBLICATIONS

Edited by the Japan Society of Ultrasonics in Medicine, Shin Choonpa Igaku, vol. 1, "Iyo Choonpa no Kiso", Igaku-Shoin Ltd., May 15, 2000, pp. 55-57.

* cited by examiner (A)

(B) (C)

(A)

(B)

ULTRASONOGRAPHIC DEVICE AND ULTRASONOGRAPHIC METHOD

TECHNICAL FIELD

This invention relates to an ultrasound diagnostic apparatus and an ultrasound diagnosing method enabling to display turbulence information together with blood flow information, the ultrasound diagnostic apparatus having a color Doppler measurement function and forming and then displaying a plurality of color Doppler images obtained by measuring a diagnosis portion of an examiner.

BACKGROUND ART

In displaying a color Doppler image, particularly in three-dimensional display, perspective information indicating a position of a blood flow whether is interior or near to a projection surface is required. Patent Literature 1 discloses a technique of displaying the perspective on a screen as a color bar by means of a gradation of luminance.
Patent Literature 1: JP-A-11-299784

In conventional color Doppler image display, when a flow like turbulence is present in a blood flow, only a portion of the blood flow around the turbulence is displayed, and the turbulence is hidden by an image of the blood flow, thereby making it difficult to find the turbulence itself. It is possible for an operator to observe turbulence present in a blood flow by arbitrarily selecting a section, but it is necessary for the operator to perform complicated operation for setting a portion in which the turbulence is present as the section.

This invention has been accomplished in view of the above circumstances, and an object thereof is to provide an ultrasound diagnostic apparatus and an ultrasound diagnosing method capable of displaying an image in which turbulence present in a blood flow is easily distinguished in the case of color Doppler image display.

DISCLOSURE OF THE INVENTION

In order to attain the above object, an ultrasound diagnostic apparatus comprises: a tomogram forming means forming a tomogram of a diagnosis portion of an examinee by transmitting/receiving an ultrasound wave to/from the examinee via an ultrasound probe; color Doppler image forming means forming a color Doppler image based on a Doppler signal obtained from the diagnosis portion; image processing means performing image processing on the tomogram and the color Doppler image; and display means displaying images obtained by the image processing means, the tomogram and the color Doppler image being color displayed on the display means, wherein the image processing means causes the color Doppler image to be displayed transparently.

The display means displays information synthesized from the color display and the transparent display. The ultrasound diagnostic apparatus further comprises selection means selecting one of the color display and the transparent display, wherein the display means displays the information selected by the selection means. The ultrasound diagnostic apparatus further comprises transparency control means controlling a degree of transparency of the color Doppler image of the transparent display.

The transparency control means controls a degree of the transparency based on the blood flow information of the color Doppler image. The transparency control means controls a degree of the transparency based on a variance of a blood flow of the color Doppler image. The transparency control means sets the transparency of the color Doppler image in such a manner that the transparency is reduced with an increase in the variance of the blood flow. The transparency control means obtains the variance as a relative value to display the color Doppler image as: an opaque image when the variance is maximum; a transparent image when the variance is null; or a semi-transparent image when the variance is not maximum nor null.

The display means displays a transparent color bar representing the transparency of the color Doppler image of the color display. The transparency control means displays the transparency color bar of which transparency is varied depending on the variance.

The ultrasound diagnostic apparatus further comprises luminance/hue control means controlling a hue of the color Doppler image of the color display, wherein the transparency control means and the luminance/hue control means control a luminance, a hue, and a transparency based on the blood flow information to create a three-dimensional color Doppler image. In addition, the ultrasound diagnostic apparatus further comprises means arranging a speed/reflection intensity and variance data of the Doppler signal in each of three-dimensional voxels in accordance with a position of each of planes and means deciding color information, luminance/hue of each of the three-dimensional voxels based on the speed and the variance, and a transparency of each of the three-dimensional voxels is decided based on the variance.

BEST MODE FOR CARRYING OUT THE INVENTION

Figure 1:
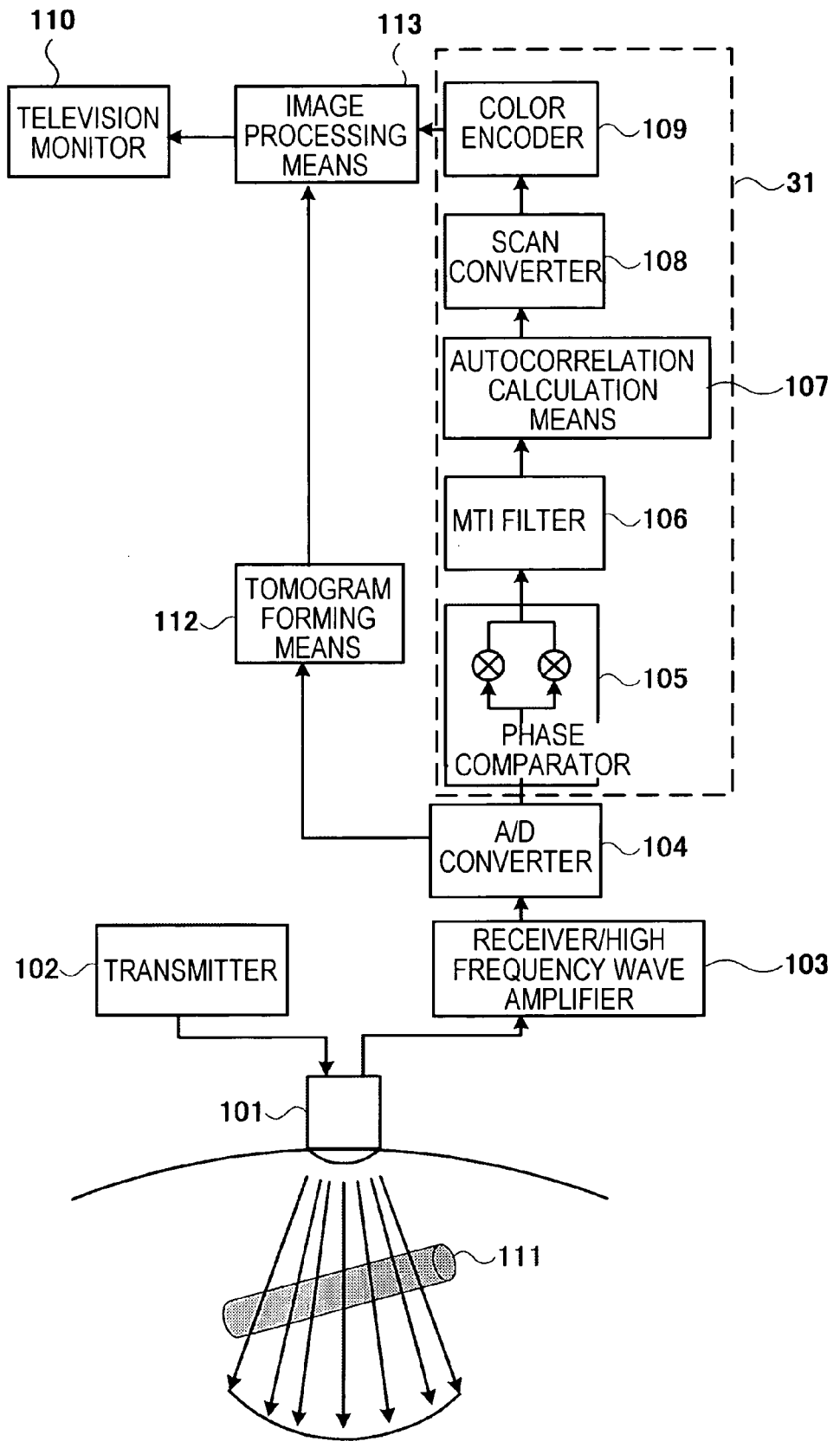
FIG. 1 An illustration of an overall constitution according to this invention.

An ultrasound diagnostic apparatus of this invention having a color Doppler measurement function will be described with reference to FIG. 1. An ultrasound pulse transmitted from a transmitter 102 is sent repeatedly from an ultrasound probe 101 to a reflection object 111 at a constant interval T. Ultrasound pulses reflected by the reflection object 111 are received by a receiving circuit 103 to be converted into digital signals by an A/D converter 104, so that digital signal outputs of a cosine component and a sine component are obtained from a phase comparator 105. A low frequency component (clatter component) the cosine component signal and the sine component signal is attenuated by a high pass MTI filter 106 so as to extract a high frequency component (blood flow component) therefrom, and then an average speed, a variance, and power of the blood flow are calculated by an autocorrelation calculation means 107. The calculation results are rearranged in accordance with a television scanning method by a digital scan converter 108, made a color corresponding to the speed and the variance by a color encoder 109, and then displayed on a television monitor 110. In the case of displaying a color Doppler image together with a tomogram, the tomogram is formed by a tomogram forming means 112 and then superimposed on the color Doppler image to be displayed on the television monitor 110 by the use of an image processing means 113.

The above-described ultrasound diagnostic apparatus captures a plurality of color Doppler images of a diagnosis portion of an examinee and displays a two-dimensional or three-dimensional image based on the color Doppler images.

Figure 2:
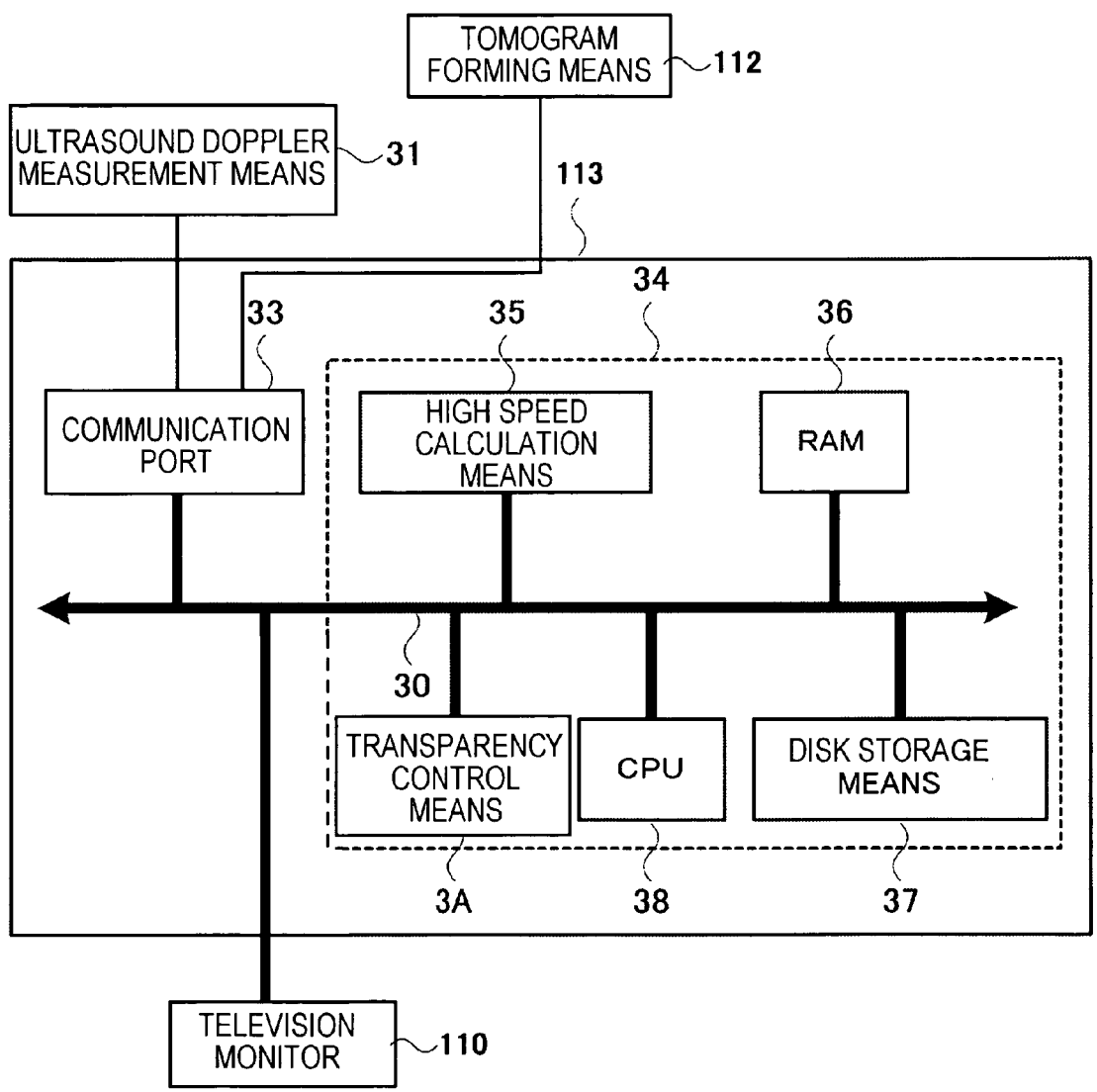
FIG. 2 An illustration of details of an image processing means according to this invention.

FIG. 2 is an illustration of details of the image processing means according to this invention. An ultrasound Doppler measurement means 31 measures a plurality of color Doppler images of a diagnosis portion of an examinee and processes the Doppler signals obtained from the ultrasound probe 101 to form a color Doppler image as shown in FIG. 1.

The image processing means 113 is provided with a communication port 33 and an image forming means 34. The communication port 33 fetches data of speeds, reflection intensities, and frequency shift variances and tomograms of the plurality of the color Doppler images measured by the ultrasound Doppler measurement means 31 into the image forming means 34. The image forming means 34 performs an image processing on the data of speeds, reflection intensities, and variances of the plurality of the color Doppler images fetched by the communication port 33 and is provided with a high speed calculator 35, a RAM 36, a disk storage means 37, a CPU 38, a transparency control means 3A. The RAM 36 and the disk storage means 37 store the fetched data of the color Doppler images. The high speed calculator 35 reads out data from the RAM 36 and the disk storage means 37 to perform a two-dimensional image processing or a three-dimensional image processing. The television monitor 110 displays a color Doppler image formed by the high speed calculator 35. The CPU 38 controls operations of the above-described components. A data bus 30 transmits data to/from the components. The transparency control means 3A appropriately controls a transparency color bar which is reduced in transparency with an increase in variance as required. A color Doppler image composed of color display and transparent display is displayed on the television monitor 110. The ultrasound diagnostic apparatus is provided with selection means (not shown) selecting one of the color display and the transparent display, and the television monitor 110 displays a color Doppler image selected by the use of the selection means.

Hereinafter, a case of performing color two-dimensional image display according to this invention will be described with reference to FIG. 3. As shown in FIG. 3(B), in the case where an overall blood flow is in a direction indicated by an arrow 4 inside a blood vessel 2 in a color two-dimensional image 6, an ultrasound beam 3 from an ultrasound probe 1 shown in FIG. 3(A) is sent to such examinee organ that has turbulence 5 present at a part of the blood flow as shown in the figure to perform a color Doppler calculation to display a color Doppler image of the organ. A data structure of the color Doppler image is such that a luminance/hue color bar 23 and a transparency color bar 24 based on a blood flow speed and a degree of variance shown in FIG. 3(C) are allotted to a portion at which the blood flow is present.

The speed, the reflection intensity, and the variance is used as information for points of the image, and, in order to perform color Doppler display corresponding to the speed and the variance, luminance/hue of each of the points is decided by the use of the luminance/hue color bar 23 based on the information of the speed and variance. Then, by the use of the transparency color bar 24, transparency of each of the points is decided based on the size of variance. The transparency color bar 24 is reduced in transparency with an increase in variance.

Turbulence present in a blood flow is generally large in variance. Therefore, since a blood flow image having a small variance becomes transparent while leaving a blood flow image having a large variance as it is, it is possible to distinguish the turbulence easily.

Hereinafter, the three-dimensional color image processing will be described. Color Doppler images of a diagnosis portion of an examinee are captured at an appropriate slice interval, and the thus-obtained color Doppler images are then stored in a three-dimensional color Doppler voxels. An arbitrary visual point and an arbitrary angle are set to the three-dimensional voxels to perform volume rendering, so that a three-dimensional color Doppler projection image is displayed on the screen. Though a luminance, a hue, a transparency of a color are decided by the use of parameters in the three-dimensional voxels in the volume rendering, the color bar used in the two-dimensional image is used in this case to decide a luminance and a hue in accordance with a speed and a variance of a blood flow, and the transparency is decided by using a value arbitrarily set by an operator. The operator can observe an arbitrary section or can control a transparency of the overall blood flow during the three-dimensional display.

Figure 4:
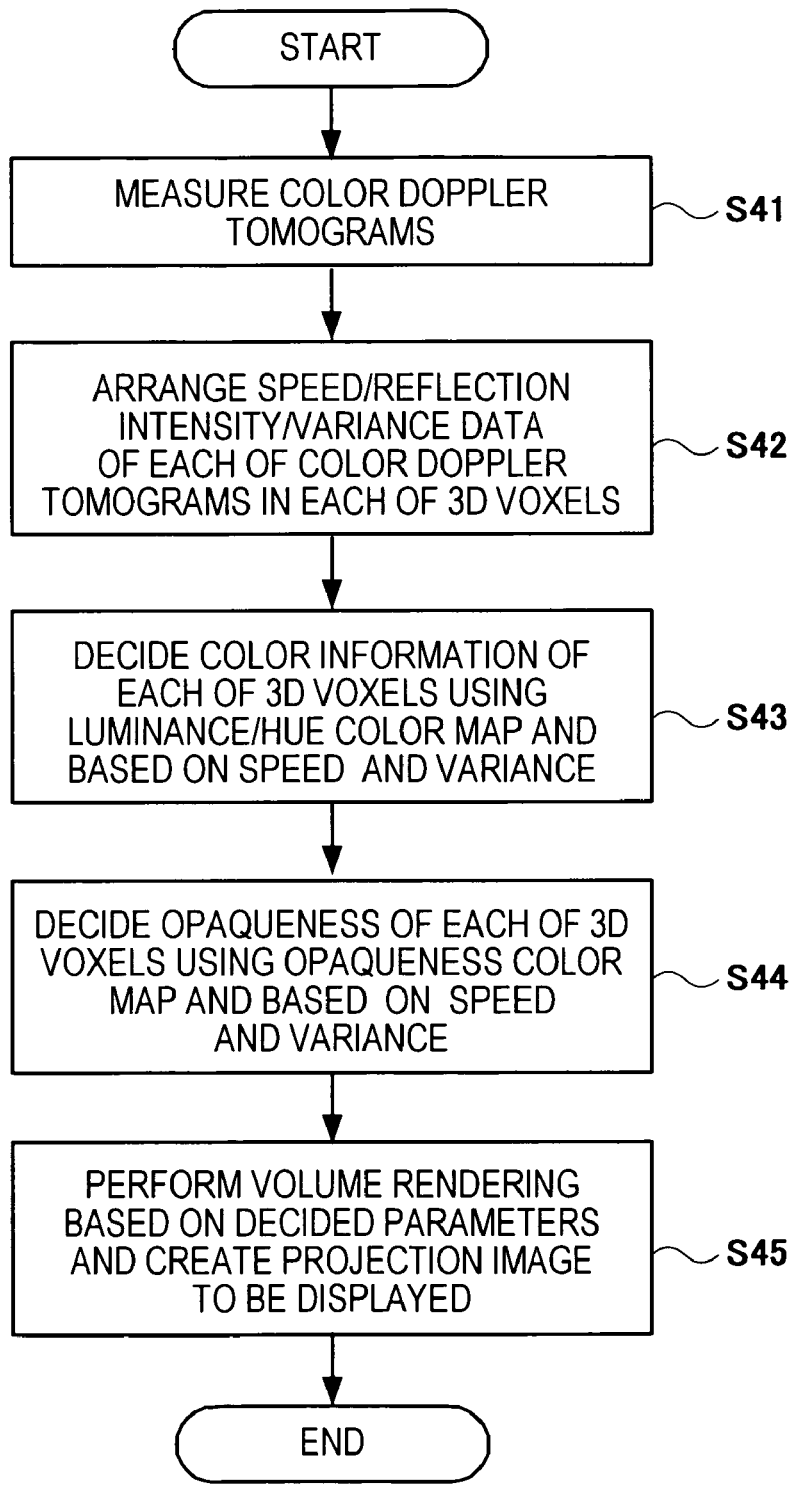
FIG. 4 An illustration of color three-dimensional image display according to this invention.
Figure 5:
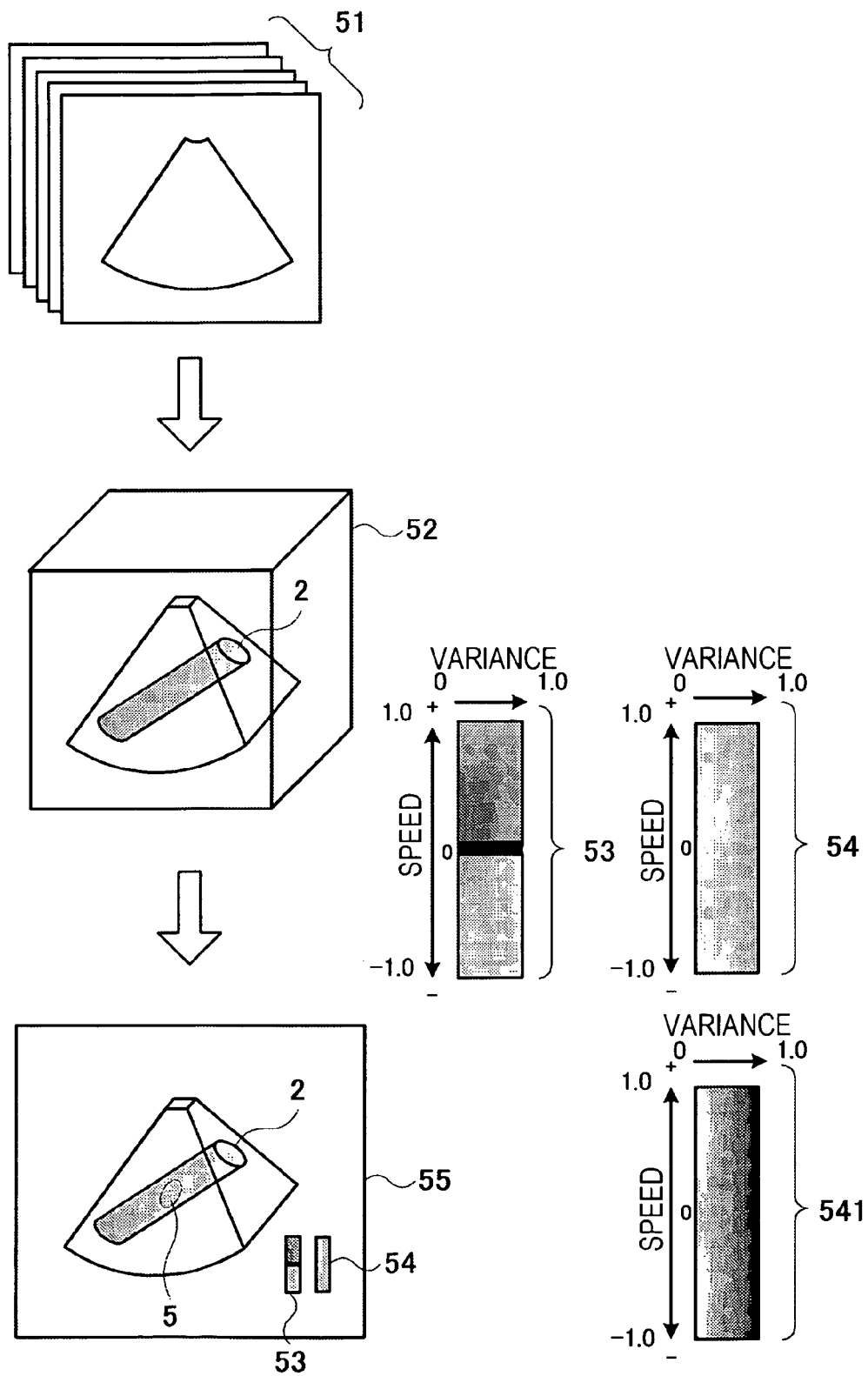
FIG. 5 An illustration of a color three-dimensional image display method according to this invention.

Hereinafter, a method of displaying a three-dimensional color Doppler image using the ultrasound diagnostic apparatus will be described with reference to FIGS. 4 and 5. FIG. 4 is a flowchart showing one example of the method of displaying a three-dimensional color Doppler image. FIG. 5 is an illustration of one example of process for displaying blood flow speed information among blood flow information on an examinee's diagnosis portion measured by the ultrasound Doppler measurement means 31 shown in FIG. 2.

In the first Step S41, color Doppler images are measured. More specifically, color Doppler images 51 (n images of P1 to Pn images) of a diagnosis portion of an examinee are measured by using the ultrasound diagnostic apparatus having the color Doppler measurement function as shown in FIG. 5.

In Step S42, a speed, reflection intensity, variance data of the measured color Doppler images are arranged in three-dimensional voxels. More specifically, each of the measured color Doppler images 51 is positioned on relevant one of three-dimensional voxels 52 in accordance with a position of a plane of the image.

In Step S43, color information of the three-dimensional voxel is decided based on the speed and the variance using a luminance/hue color bar. More specifically, the speed, the reflection intensity, and the variance are used as information of each of points on the three-dimensional voxels 52 as shown in FIG. 5, and, in order to perform color Doppler display in accordance with the speed and the variance, the luminance/hue of each of the points on the three-dimensional voxels 52 is decided by using the luminance/hue bar 53 based on the information of the speed and the variance.

In Step S44, the transparency of each of the three-dimensional voxels is decided based on the variance using a transparency color bar 54. More specifically, as shown in FIG. 5, the transparency of each of points on the three-dimensional voxels 52 is decided by using the transparency color bar 54. Transparency of the transparency color bar 54 is reduced with an increase in the variance. The transparency color bar 54 is not more than one example, and a different transparency color bar can be selected by the transparency control means 3A. For instance, there may be used a transparency color bar which is increased in transparency for a portion where the variance is relatively small and reduced in transparency (increased in opaqueness) for a portion where the variance is increased as compared to the transparency color bar 54. That is, the transparency control means 3A selects one of the transparency color bars 54 which vary in proportion of transparency changing in accordance with the variance. The transparency may be controlled by arbitrarily performing calculation on the transparency obtained by the transparency color bar 54 in place of selecting the transparency color bar 54.

In Step S45, volume rendering is executed based on the parameter decided in the foregoing processing to create a projection image, thereby displaying the projection image. More specifically, as shown in FIG. 5, the volume rendering is performed on the three-dimensional voxel 52 to create a three-dimensional color Doppler projection image 55, and the three-dimensional color Doppler projection image 55 is displayed on the television monitor 110.

As a result, as shown in FIG. 5, a blood flow having a small variance is increased in transparency, and a blood flow having a large variance is reduced in transparency (increased in opaqueness), so that turbulence is emphasized in the displayed three-dimensional color Doppler projection image 55.

The speed and the variance shown in FIG. 5 are obtained as relative values. For example, a speed component is represented by a numerical value of from −1.0 to 1.0, and a variance component is represented by a numerical value of from 0 to 1.0. In the case where the speed is +1.0 and the variance is 0, color information of the three-dimensional voxel is set to red and transparent, and then a three-dimensional color Doppler projection image 55 is created by performing volume rendering to display the transparent red on the television monitor 110. In the same manner, in the case where the speed is +1.0 and the variance is 1.0, color information of the three-dimensional voxel is set to yellow and not transparent. Also, in the case where the speed is −1.0 and the variance is 0.5, color information of the three-dimensional voxel is set to yellow green and semi-transparent.

Figure 6:
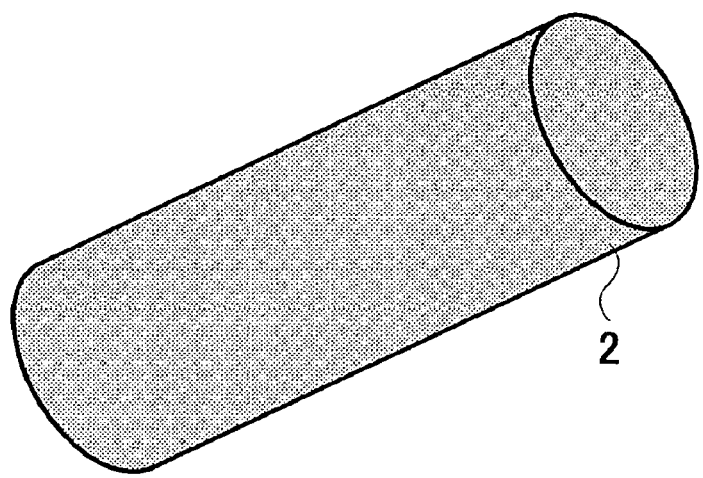
FIG. 6 An illustration of a display result according to this invention.
Figure 6:
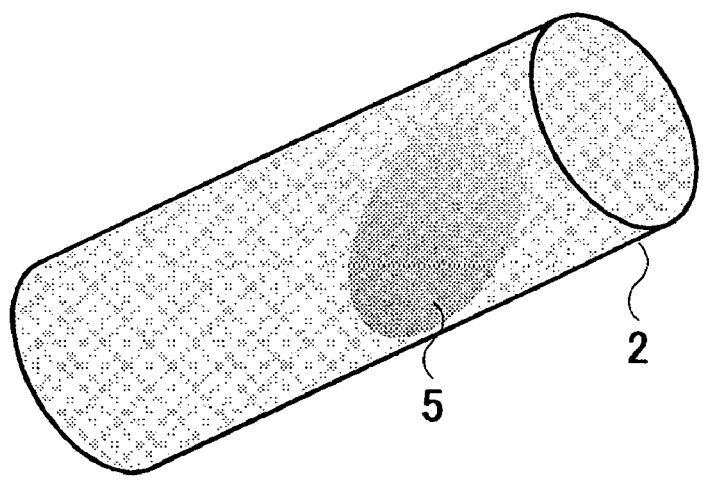

According to this embodiment, in a three-dimensional color Doppler projection image created by arranging color Doppler images measured by the ultrasound diagnostic apparatus in three-dimensional voxels and then performing volume rendering, an ordinary blood flow having a smaller variance has a greater transparency, and turbulence having a larger variance is displayed opaque. Therefore, in the case of the blood flow in which the turbulence is observed at a part thereof as shown in FIG. 5, a turbulence 5 present in a blood flow is distinguished easily because a blood flow in the blood vessel 2 having a smaller variance is transparent according to this invention as shown in FIG. 6(B), though the turbulence 5 has been hidden by the blood flow having a smaller variance in the blood vessel 2 with the conventional method as shown in FIG. 6(A). Thus, it is possible to achieve effective display for image diagnosis in ultrasound diagnostic apparatuses having color Doppler measurement function.

Though the case of processing the luminance/hue color bar 53 and the transparency color bar 54 separately from each other is described in the foregoing, a color bar 541 may be synthesized from the luminance/hue color bar 53 and the transparency color bar 54 to perform the processing on the color bar 541. The luminance/hue color bar 53 and the transparency color bar 54 may be displayed together with the three-dimensional color Doppler projection image 55 as shown in FIG. 5. The simultaneous display of the luminance/hue color bar 53, the transparency color bar 54, and the three-dimensional color Doppler projection image 55 is useful as a reference in observation and facilitates perception of a degree of turbulence.

Also, selection means (not shown) for selecting one of the luminance/hue color bar 53 and the transparency color bar 54 may be provided for switching alternately the luminance/hue color bar 53 and the transparency color bar 54 to display only the selected color bar. Further, the luminance/hue color bar 53 and the transparency color bar 54 may be used simultaneously for display. In the case of using the transparency color bar 54 only, display may be such that red is used for representing the luminance/hue and the transparency of red is changed. Therefore, by setting the transparency in such a manner that the transparency is reduced in a portion having a large variance and is increased in a portion having a small variance and displaying each point with red, it is possible to display turbulence with red of less transparency while displaying other portions with red of greater transparency.

Figure 3:
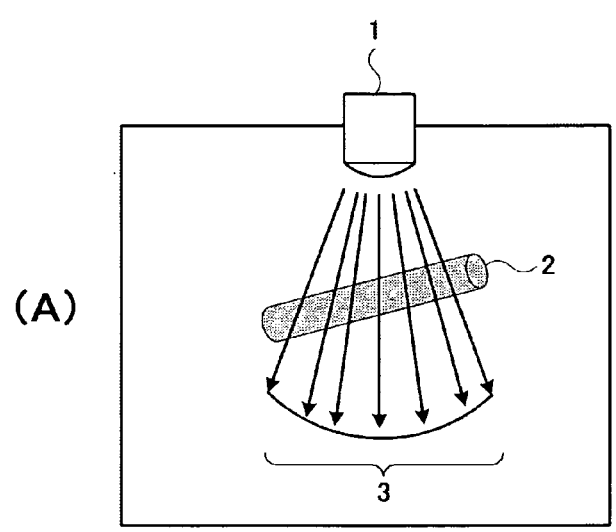
FIG. 3 An illustration of color two-dimensional image display according to this invention.
Figure 3:
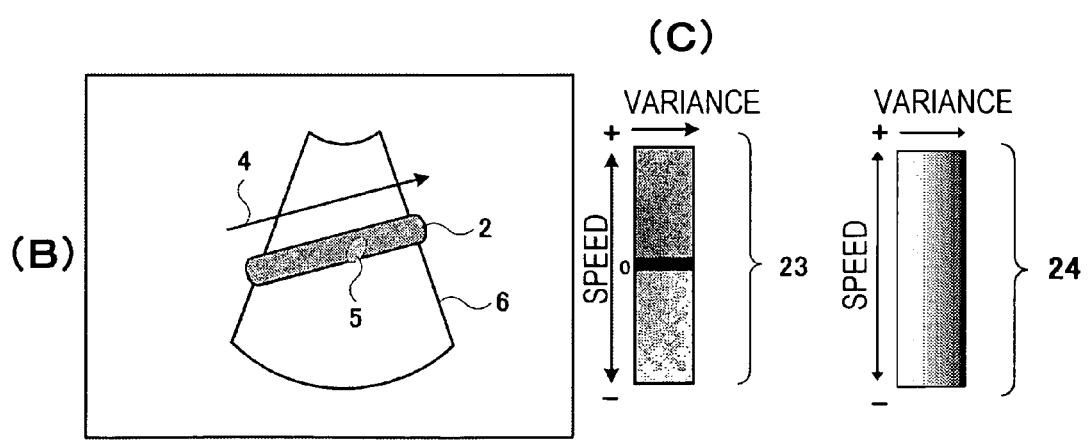

Though the color bars 23 and 53 are shown as monochromatic bars in FIGS. 3 and 5, they are color displayed in practice. In the color bars 23 and 53, a portion close to the speed of 0 is close to black, and the color changes gradually from dark red to orange and then to yellow gradually in accordance with the increase in variance in the case of the speed in the positive direction. In the case of the speed in the negative direction, the color changes gradually from dark blue to light blue and then to green in accordance with the increase in variance. The color of the blood vessel 2 in the color Doppler projection image is displayed by the use of the color corresponding to the color bars 23 and 53. Therefore, in the case where the turbulence 5 is present at a part of the blood flow generally flowing at the speed in the direction indicated by an arrow 4 as shown in FIG. 3(B), the blood flow in the blood vessel 2 is generally displayed with a reddish color and the turbulence 5 is displayed with a greenish color.

Though the color of luminance/hue color bar 53 is decided as shown in FIGS. 3 and 5, any color may be used for the colors of the color bar corresponding to the speed and the variance.

The invention claimed is:

1. An ultrasound diagnostic apparatus comprising:
a tomogram forming unit for forming a tomogram of a diagnosis portion of an examinee by transmitting/receiving an ultrasound wave to/from the examinee via an ultrasound probe;
color Doppler image forming unit for forming a color Doppler image based on a Doppler signal obtained from the diagnosis portion;
a transparency control unit for controlling a degree of the transparency of the color Doppler image;
an image processing unit for performing image processing on the tomogram and the color Doppler image;
a display unit for displaying images obtained by the image processing unit, the tomogram and the color Doppler image being color displayed on the display unit,
selection unit for selecting one or both of a luminance/hue color bar, which is based on the information of a velocity and/or variance of a blood flow, and/or a transparency color bar from a plurality of transparency color bars, which is based on the information of the variance, for alternatively or simultaneously displaying the luminance/hue color bar and/or the transparency color bar on the display unit; and
wherein the transparency control unit for controlling a degree of transparency changes the relationship between the transparency and the variance, and changes the degree of transparency of the color Doppler image based on the changed relationship in accordance with the one transparency color bar selected by the selection unit,
the image processing unit causes the color Doppler image to be displayed transparently, based on the changed degree of transparency, and
the display unit displays at most the one transparency color bar selected by the selection unit.

2. The ultrasound diagnostic apparatus according to claim 1, wherein the display unit displays information composed of the color display and the transparent display.

3. The ultrasound diagnostic apparatus according to claim 1, further comprising a second unit for selecting one of the color display and the transparent display, wherein the display unit displays the information selected by the second unit for selecting.

4. The ultrasound diagnostic apparatus according to claim 1, wherein the transparency control unit controls a degree of the transparency based on blood flow information of the color Doppler image.

5. The ultrasound diagnostic apparatus according to claim 1, wherein the transparency control unit controls a degree of the transparency based on a variance of a blood flow of the color Doppler image.

6. The ultrasound diagnostic apparatus according to claim 1, wherein the transparency control unit sets the transparency of the color Doppler image in such a manner that the transparency is reduced with an increase in a variance of the blood flow.

7. The ultrasound diagnostic apparatus according to claim 1, wherein the transparency control unit obtains the variance as a relative value to display the color Doppler image as: an opaque image when the variance is maximum; a transparent image when the variance is null; or a semi-transparent image when a variance is not maximum nor null.

8. The ultrasound diagnostic apparatus according to claim 1, wherein the display unit displays a transparent color bar representing the transparency of the color Doppler image of the color display.

9. The ultrasound diagnostic apparatus according to claim 1, further comprising a luminance/hue control unit for controlling a hue of the color Doppler image of the color display, wherein the transparency control unit and the luminance/hue control unit for controlling a hue controls a luminance, a hue, and a transparency based on the blood flow information to create a three-dimensional color Doppler image.

10. The ultrasound diagnostic apparatus according to claim 9, further comprising:
   an arranging unit for arranging a speed/reflection intensity and variance data of the Doppler signal in each of three-dimensional voxels in accordance with a position of each of planes;
   a luminance/hue deciding unit for deciding a luminance/hue of each of the three-dimensional voxels based on the speed and a variance; and
   a transparency deciding unit for deciding a transparency of each of the three-dimensional voxels based on the variance.

11. The ultrasound diagnostic apparatus according to claim 9, wherein the display unit displays a turbulence portion of the blood flow of the three-dimensional color Doppler image.

12. The ultrasound diagnostic apparatus according to claim 1, wherein the color Doppler image forming unit comprises:
   a phase comparator outputting a cosine component and a sine component of the Doppler signal;
   an MTI filter damping a low frequency component of the cosine component signal and the sine component signal and extracting a high frequency component of the cosine component signal and the sine component signal;
      an autocorrelation calculation unit calculating an average speed, a variance, and power of the blood flow;
      a digital scan converter rearranging in accordance with a television scanning method; and
      a color encoder performing colorization corresponding to the speed and the variance.

13. The ultrasound diagnostic apparatus according to claim 1, comprising a luminance/hue display unit for displaying a luminance/hue color bar representing a color of the color Doppler image of the color display,
   wherein the luminance/hue color bar changes in color in such a manner that: black is displayed at a portion corresponding to the blood flow speed of 0; the change in the case of a positive direction speed is displayed as a gradual change from dark red to orange and then to yellow in accordance with the increase in variance; and the change in the case of a negative direction speed is displayed as a gradual change from dark blue to light blue and then to green in accordance with the increase in variance.

14. The ultrasound diagnostic apparatus according to claim 1, wherein the image processing unit comprises a storage unit for storing data of a plurality of color Doppler images and reads out the data from the storage unit to perform the image processing on the data of speeds, reflection intensities, and variances of the plurality of the color Doppler images.

15. The ultrasound diagnostic apparatus according to claim 1, wherein the plurality of color Doppler images are acquired and subjected to volume rendering so as to create a projection image to be displayed.

16. The ultrasound diagnostic apparatus according to claim 15, further comprising:
   a measuring unit for measuring a plurality of color Doppler images;
   an arranging unit for arranging speed/reflection intensity and variance data of the color Doppler images in each of three-dimensional voxels corresponding to each of planes;
   a luminance/hue deciding unit for deciding color information a luminance/hue of each of three-dimensional voxels based on the speed and the variance;
   a transparency deciding unit for deciding a transparency of each of the three-dimensional voxels based on the variance; and
   a rendering unit for performing volume rendering based on parameters decided by the foregoing steps and creating a projection image to be displayed.

17. An ultrasound diagnosing method comprising the steps of:
   transmitting/receiving an ultrasound wave to/from an examinee via an ultrasound probe;
   forming a tomogram of a diagnosis portion of the examinee;
   forming a color Doppler image based on a Doppler signal obtained from the diagnosis portion;
   selecting one or both of a luminance/hue color bar, which is based on the information of a velocity and variance of a blood flow, and/or a transparency color bar from a plurality of transparency color bars, which is based on the information of the variance, for alternatively or simultaneously displaying the luminance/hue color bar and/or the transparent color bar on the display means;
   performing image processing on the tomogram and the color Doppler image based on the result of the selecting step;
   displaying the images which underwent the image processing so as to display the tomogram and the color Doppler image in color display; and
   displaying the color Doppler image transparently which includes a step for controlling a degree of the transparency of the color Doppler image of the transparent display, wherein the step of selecting further comprises the steps of:
- selecting one of the transparency color bars,
- changing the relationship between the transparency and the variance, and
- changing the degree of transparency of the color Doppler image based on the changed relationship.

18. The ultrasound diagnosing method according to claim 17, further comprising the steps of:
- measuring a plurality of color Doppler images;
- arranging speed/reflection intensity and variance data of the color Doppler images in each of three-dimensional voxels corresponding to each of planes;
- deciding color information of a luminance/hue of each of three-dimensional voxels based on the speed and the variance;
- deciding a transparency of each of the three-dimensional voxels based on the variance; and
- performing volume rendering based on parameters decided by the foregoing steps and creating a projection image to be displayed.

* * * * *